(12) United States Patent
Karbowniczek et al.

(10) Patent No.: US 8,052,707 B2
(45) Date of Patent: Nov. 8, 2011

(54) PATIENT'S SKIN PUNCTURING DEVICE

(75) Inventors: Jacek Karbowniczek, Warsaw (PL); Wojciech Sarna, Warsaw (PL); Andrzej Jankowski, Warsaw (PL); Wojciech Wyszogrodzki, Warsaw (PL); Andrzej Czernecki, Warsaw (PL)

(73) Assignee: "HTL-Strefa" Spolka Akcyjna, Ozorkow (PL)

( * ) Notice: Subject to any disclaimer, the term of this patent is extended or adjusted under 35 U.S.C. 154(b) by 155 days.

(21) Appl. No.: 12/530,400

(22) PCT Filed: Apr. 18, 2008

(86) PCT No.: PCT/PL2008/000030
§ 371 (c)(1),
(2), (4) Date: Sep. 8, 2009

(87) PCT Pub. No.: WO2008/130259
PCT Pub. Date: Oct. 30, 2008

(65) Prior Publication Data
US 2010/0168775 A1    Jul. 1, 2010

(30) Foreign Application Priority Data

Apr. 19, 2007   (PL) .......................... 382235

(51) Int. Cl.
*A61B 5/151*  (2006.01)
(52) U.S. Cl. ...................................... 606/182

(58) Field of Classification Search .......... 606/181–183, 606/167, 184, 185; 600/573–584
See application file for complete search history.

(56) References Cited

U.S. PATENT DOCUMENTS

| 4,527,561 | A | * | 7/1985 | Burns .......................... 606/182 |
| 5,356,420 | A | * | 10/1994 | Czernecki et al. ............ 606/182 |
| 6,858,015 | B2 | * | 2/2005 | List ................................ 600/583 |
| 2004/0249406 | A1 | | 12/2004 | Griffin et al. |
| 2004/0260326 | A1 | | 12/2004 | Lipoma et al. |

FOREIGN PATENT DOCUMENTS
WO    WO 2007/005665 A1    1/2007

OTHER PUBLICATIONS
International Search Report Dated Sep. 2, 2008.
* cited by examiner

*Primary Examiner* — Kathleen Sonnett
(74) *Attorney, Agent, or Firm* — Plumsea Law Group, LLC

(57) ABSTRACT

A patient's skin puncturing device, particularly for collecting a blood sample for diagnostic purposes, including a housing, a lancet slidably positioned inside the housing and having a body with a sheathed puncturing needle seated therein, and a push button positioned at the one end of the housing. Between a face end of the push button and the lancet body a drive spring is placed, and between the other end of the housing, which is provided with an opening for the puncturing needle, and the lancet body a return spring is placed. Between the housing and the lancet body is placed a lancet actuation lock, preferably in the form of interlocks of a washer. The device has a drive spring catch, preferably in the form of grabs of the washer, to preclude the drive spring from following the lancet in the puncture phase and in the retraction phase of the lancet.

13 Claims, 3 Drawing Sheets

PATIENT'S SKIN PUNCTURING DEVICE

TECHNICAL FIELD

The subject of the invention is a patient's skin puncturing device, particularly for collecting blood samples for diagnostic purposes.

BACKGROUND ART

From the patent specification U.S. Pat. No. 5,356,420 the puncturing device is known comprising a sleeve and a push button positioned at one sleeve end. The other sleeve end terminates with a bottom with an opening therein. Inside the sleeve a piston is slidably positioned, terminating with a push rod at the end closer to the push button, and with a puncturing needle at the end closer to the bottom opening. Inside the sleeve, between the push button face and the piston a drive spring is located, and between the piston and the sleeve bottom a return spring is placed. The piston comprises locking means of an actuation of the piston with the puncturing needle, which is located on an outer perimeter of the piston and is in the form of wings resting on an internal projection of the sleeve. When the device is used, the push button is pressed down by an user, which causes the drive spring compression until the moment when the piston actuation locking means is broken off and the piston with the puncturing needle starts to move along the sleeve towards the bottom opening. Thus, the wings get broken and a subsequent re-use of the device is not possible.

In the patent specification U.S. Pat. No. 6,248,120 is disclosed the patient's skin puncturing device in which, in one of its embodiments, an additional structure element in the form of a washer is provided. The washer comprises locking means of an actuation of a piston with a puncturing needle, which protects the device against its actuation until the moment when a push button is pressed down and the piston actuation locking means is broken off.

In the up to now known puncturing devices, in a puncture phase a free end of the drive spring drives a puncturing assembly and follows it, and in the puncture phase and in a retraction phase of the puncturing assembly a gravity force of the drive spring and a force deriving from dynamic drive spring expansion affect the puncturing assembly. In the puncture phase, these forces displace the puncture assembly along a housing to the opening for the puncture needle. In the retraction phase of the puncturing assembly, these forces affect the puncturing assembly back in the reaction to the puncturing assembly impacts into the drive spring free end. These impacts induce unfavourable dynamic drive spring tensions and cause that the puncture assembly, quick-retracting under the influence of the return spring, bounces from the expanded drive spring.

In the known puncturing devices, it is observed a disadvantageous effect of multiple skin puncture as a consequence of series of successive rebounds of the puncturing assembly from the drive spring. During these rebounds of the puncturing assembly a tip of the puncturing needle penetrates into a wound. The rebounds accompany with the puncturing device vibrations which are adverse for the user's and/or patient's feelings.

DISCLOSURE OF INVENTION

The purpose of the present invention is to provide a disposable patient's skin puncturing device for collecting blood sample for diagnostic purposes, which is cheap, safe, both for the patient and for the service personnel and easy in use.

Particularly, the purpose of this invention is to provide the patient's skin puncturing device with the structure which enables to reduce a pain being felt by the patient during the skin puncture and to retract very quickly the puncturing needle tip from the skin after puncture for enhancing a comfort of puncturing device application.

The next purpose of this invention is to provide the patient's skin puncturing device of the structure which enables to eliminate unfavourable effect of the multiple skin puncture present in the known puncturing devices in the puncture phase as well as in the retraction phase of the piston with the puncturing needle or other puncturing assembly into the inside of the housing, whereas this effect is caused by rebounding the puncturing assembly from the drive and return springs at least one end of which is free.

The essence of the patient's skin puncturing device according to the present invention comprising a housing, a lancet slidably positioned inside the housing and having a lancet body with a sheathed puncturing needle seated therein, and a push button positioned at one end of the housing, whereas between a face end of the push button and the lancet body a drive spring is placed, and between the housing other end with an opening for the puncturing needle and the lancet body a return spring is placed, and between the housing and the lancet body lancet actuation locking means is placed, is that it has drive spring catching means to preclude the drive spring from following the lancet in the puncture phase and in the retraction phase of the lancet.

Preferably, drive spring catching means is integrally formed with an element of the puncturing device, which is chosen from the housing and the push button.

Preferably, drive spring catching means is integrally formed with an additional separate element of the puncturing device.

Preferably, drive spring catching means and lancet actuation locking means are formed on the same element of the puncturing device.

Preferably, the elements of the puncturing device have dimensions and mutual arrangement, which maintain the drive spring after the skin puncture in a tense condition.

The advantage of the patient's skin puncturing device according to the invention is the simplicity of its structure with a small number of the elements, which structure enables to obtain a disposable patient's skin puncturing device for collecting blood sample for diagnostic purposes, which is cheap, safe, both for the patient and for the service personnel and easy in use.

The next advantage of the patient's skin puncturing device according to the invention is that its structure enables quicker withdrawal of the lancet due to the fact that the lancet load by forces originating from the drive spring in the lancet retraction phase into the inside of the housing after the skin puncture is removed.

The further advantage of the patient's skin puncturing device according to the invention is that its structure eliminates the disadvantageous effect of the multiple skin puncture due to lengthening the distance which is covered by the lancet with the puncturing needle in the retraction phase into the inside of said housing until the moment of the impact into said drive spring as well as due to the restriction of the drive spring action onto the lancet insofar the drive spring movement is in the puncture phase, from a certain moment, locked and the drive spring, in the preferred embodiment of the invention, can remain in the retraction phase in the partial tense condition.

In the present puncturing device, the lancet with the puncturing needle is much quicker withdrawn into the inside of the housing after the skin puncture because the return spring does not have to overcome the drive spring weight and only the weight of the lancet body with the puncturing needle. The locking of the drive spring eliminates also the disadvantageous effect of the multiple skin puncture as well as vibrations of the lancet body together with the puncturing needle as a result of body forces and drive spring vibrations.

BRIEF DESCRIPTION OF DRAWINGS

The subject of the invention is shown in the example embodiment in the drawings, where.

BEST MODE OF CARRYING OUT THE INVENTION

Figure 1:
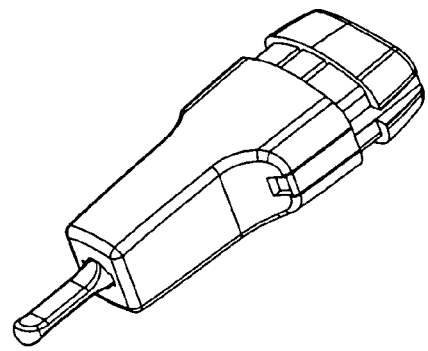
FIG. 1 shows the perspective view of the patient's skin puncturing device according to the invention, before its use, FIG. 2—the exploded view of the device of FIG. 1, FIG. 3—the longitudinal views of the device of FIG. 1, before its activation, FIG. 4—the longitudinal views of the device of FIG. 1, after removal of the sheath from the puncturing needle, FIG. 5—the longitudinal views of the device of FIG. 1, with the push button preliminary pressed down and at full tension of the drive spring, FIG. 6—the longitudinal views of the device of FIG. 1, with the push button fully pressed down and after breaking lancet actuation locking means off, FIG. 7—the longitudinal views of the device of FIG. 1, in the moment of the patient's skin puncture when the drive spring is caught by the drive spring catching means, the return spring is compressed and the puncturing needle protrudes from an opening for the puncturing needle with the full puncture depth, FIG. 8—the longitudinal views of the device of FIG. 1, after the puncture when the lancet with the puncturing needle is withdrawn by the return spring inwards the housing while the drive spring is caught by the drive spring catching means and is locked in a partial tense condition, FIG. 9—the perspective view, in enlargement, of the internal elements of the device, that is the lancet with the puncturing needle, the washer and the drive spring before the device activation, and FIG. 10—the perspective view, in enlargement, of the internal elements of the device, that is the lancet with the puncturing needle, the washer and the drive spring in the puncture moment with the drive spring caught by and locked by the catching means.
Figure 2:
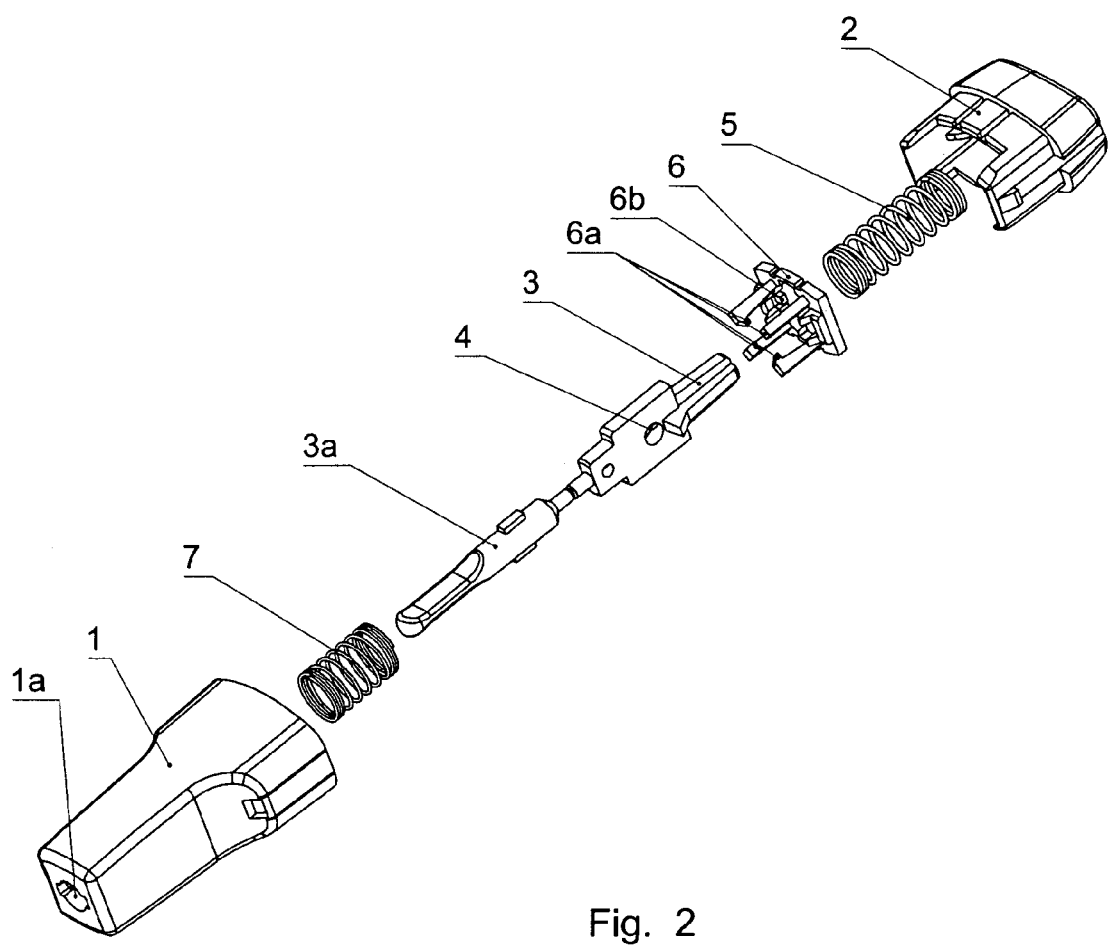

The patient's skin puncturing device according to the one of the preferred embodiments of the invention, as shown in the drawings, is comprised of a housing 1 and a push button 2 mounted on the one of ends of the housing 1. The other end of the housing 1 has an opening 1a for a puncturing needle 4. In the housing 1a lancet is positioned, which is longitudinally movable. The lancet has a body 3 in which the puncturing needle 4 is seated. The puncturing needle 4 has a tip protected by a sheath 3a which is removed before use of the device. A drive spring 5 is arranged between the lancet body 3 and the internal side of the face end of the push button 2. A return spring 7 is placed inside the housing 1 between the lancet body 3 and the other end of the housing 1, in which the opening 1a is made for the puncturing needle 4. In the housing 1, between the drive spring 5 and the lancet a washer 6 is placed. The washer 6 comprises lancet actuation locking means in the form of interlocks 6b for the lancet and drive spring catching means in the form of grabs 6a for the drive spring 5.

Figure 3:
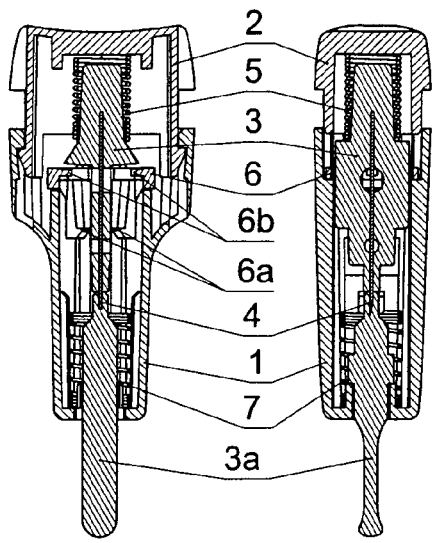

FIG. 3 presents the device, according to the invention, before the activation, with the sheath 3a breakably connected with the lancet body 3 after formation together with the body 3 in the technological process so that the required sterility of the puncturing needle tip is completely guaranteed.

Figure 4:
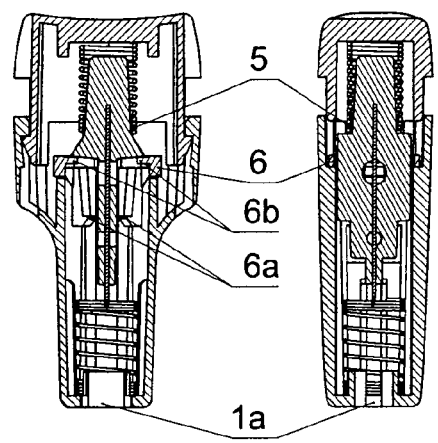
Figure 5:
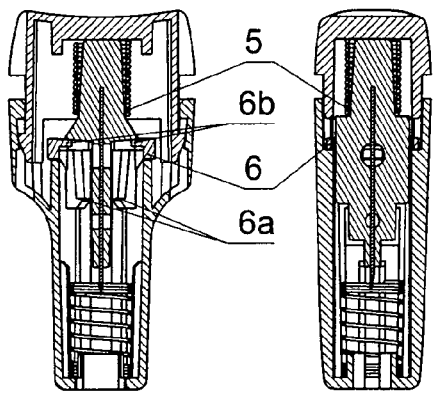
Figure 6:
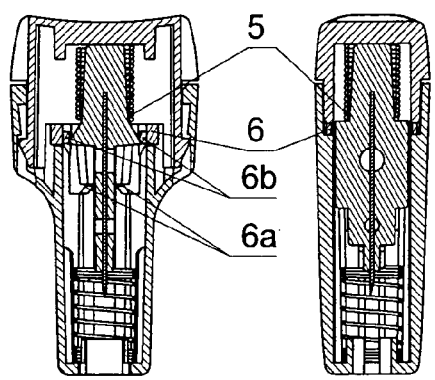
Figure 7:
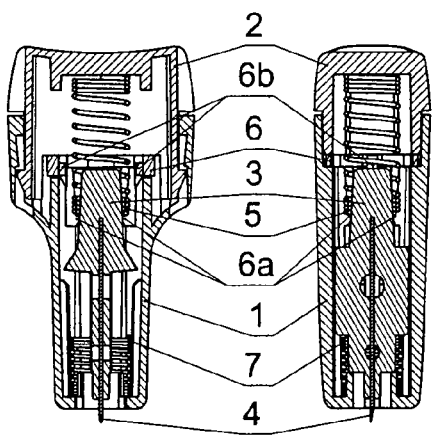
Figure 8:
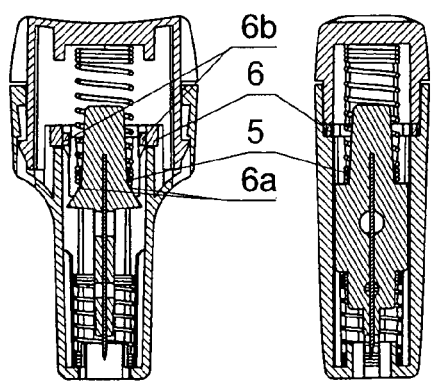

As shown in FIG. 4, before the use of the puncturing device the sheath 3a should be twisted and removed to uncover the tip of the puncturing needle 4. Then, as a result of the thrust force applied by the user to the external side of the face end of the push button 2, the push button 2 is pressed down causing the full tension of the drive spring 5 and then breaking off lancet actuation locking means that is the interlocks 6b, as it is presented in FIGS. 5 and 6. Due to energy imparted from the push button 2 and under the influence of the expanding drive spring 5, the lancet in this moment starts to move towards the opening 1a and performs the puncture phase. The drive spring 5 expands until the moment when it is elongated so that its free end abuts against the drive spring catching means that is against the grabs 6a with which is provided the washer 6 constituting an additional separate structure element of the device. From that moment, the drive spring 5 is locked between the internal side of the face end of the push button 2 and the grabs 6a for the drive spring 5, and then the drive spring 5 does not expand more and does not move. The lancet body 3 together with the puncturing needle 4 moves further inside the housing 1 until the moment when the body 3 rests upon an internal abutting surface of the housing 1. In that moment, the puncturing needle 4 extends away from the housing 1 with the maximal puncture depth, as show in FIG. 7. The return spring 7 is then compressed between the internal surface of the housing 1 and the lancet body 3. Next, as shown in FIG. 8, the return spring 7 expands causing the retraction of the lancet body 3 together with the puncturing needle 4 into the inside of the housing 1 until the moment when the tip of the puncturing needle 4 is completely withdrawn inwards the housing 1. In this way, the device performs the retraction phase of the lancet, whereas the lancet is quickly retracted into the inside of the housing 1 insofar the lancet is not loaded by forces generated in the drive spring 5 which is locked by the grabs 6a of the washer 6 in the partial tense condition. The partial tense condition means that the drive spring 5 has the tension lower than the tension in the preliminary tense condition before the device activation and lower than the full tension only just before breaking the interlocks 6b off and before the lancet actuation. The distance which covers the lancet with the puncturing needle 4 during retraction into the inside of the housing 1 until the moment of its impact into the drive spring 5 is long enough so that disadvantageous rebounds of the lancet from the drive and return springs, respectively, 5 and 7 during the lancet withdrawal by the return spring 7 inwards the housing 1 are eliminated or restricted sufficiently to eliminate the effect of the multiple skin puncture. The skin pain is reduced to minimal, inevitable and necessary to puncture the skin for collecting the blood sample. Further, excessive vibrations of the lancet in consequence of body forces and the vibrations of the drive spring 5 as well as in consequence of the lancet rebounds from the drive and the return springs, respectively, 5 and 7, are also eliminated. This contributes to the increase of the comfort of the application of the puncturing device according to the present invention.

Figure 9:
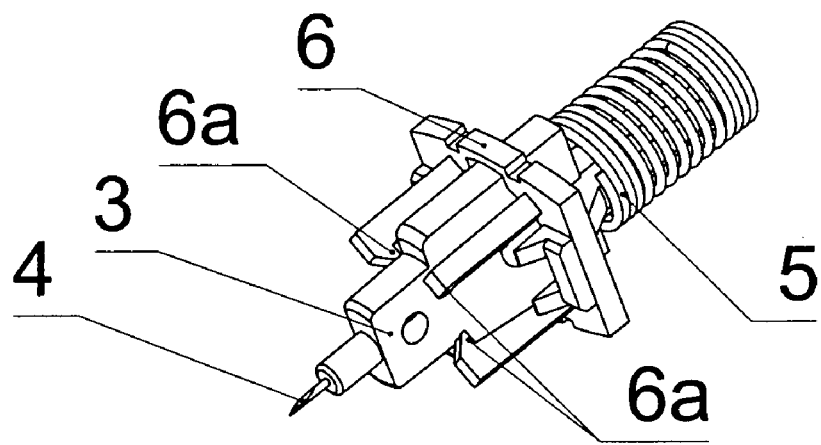

In the described preferred embodiment of the puncturing device according to the present invention, the grabs 6a for the drive spring 5 are made as the structure elements integral with the additional separate element of the device, which is the washer 6 and which simultaneously is provided with the lancet actuation locking means. In this embodiment of the invention, the lancet actuation locking means constitutes the interlocks 6b for the lancet, as shown in enlargement in FIGS. 9 and 10.

In other embodiments of the puncturing device according to the present invention, the drive spring catching means, preferably in the form of the grabs 6a for the drive spring 5, can be integral with the housing 1 or with the push button 2.

Figure 10:
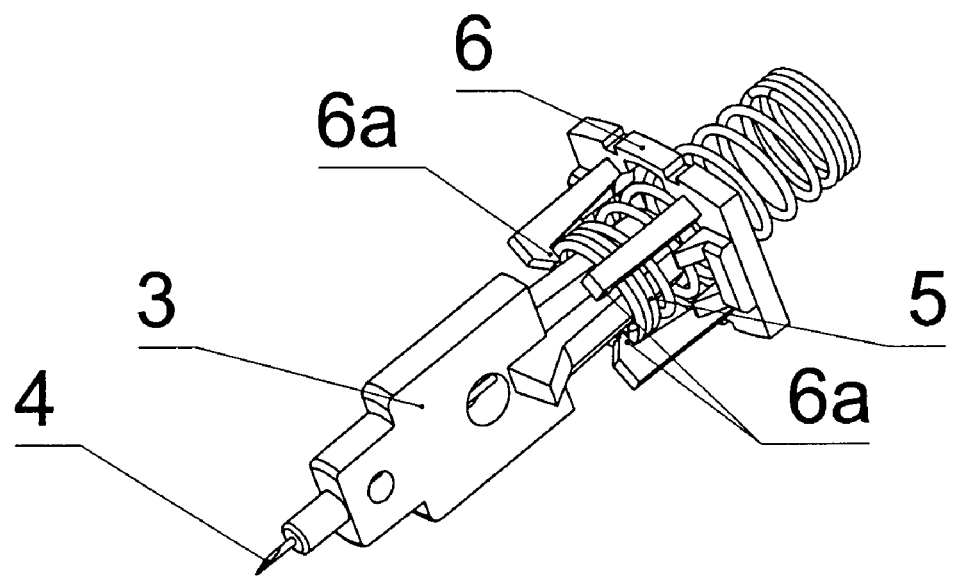

Moreover, in the described preferred embodiment of the patient's skin puncturing device according to the present invention, the structure elements have such dimensions matched to each other and are arranged in such mutual configuration that after the skin puncture the drive spring 5 remains in the partial tense condition, as shown in enlargement in FIG. 10.

Thus, in the case when the lancet yet bounces against the drive spring 5 during the withdrawal into the inside of the housing 1, the back reaction of the drive spring 5 onto the lancet would be significantly reduced.

LIST OF THE STRUCTURE ELEMENTS OF THE DEVICE

1 . . . the housing
1a . . . the opening for the puncturing needle
2 . . . the push button
3 . . . the lancet body
3a . . . the sheath of the puncturing needle tip
4 . . . the puncturing needle
5 . . . the drive spring
6 . . . the washer
6a . . . the grabs for the drive spring
6b . . . the interlock for the lancet
7 . . . the return spring

We claim:

1. A patient's skin puncturing device, for collecting a blood sample for diagnostic purposes, comprising:
   a housing having a first end and a second end,
   a lancet slidably positioned inside said housing and having a body with a sheathed puncturing needle seated therein, and
   a push button positioned at end of said housing,
   whereas between a face end of said push button and said lancet body a drive spring is placed as directly contacting said face end of said push button at a first end of said drive spring and contacting said lancet body at a second end of said drive spring, and
   between the second end of said housing, which is provided with an opening for said puncturing needle, and said lancet body a return spring is placed, and
   between said housing and said lancet body a lancet actuation locking means is placed, and
   for precluding said drive spring from following said lancet in a puncture phase and in a retraction phase of said lancet said puncturing device has a drive spring catching means which is integrally formed with an additional separate element of said puncturing device,
   wherein the second end of the drive spring is spaced apart from the drive spring catching means at a start of the puncture phase,
   wherein said drive spring contacts said lancet body during the start of the puncture phase, pushes said lancet body in a longitudinal puncturing direction during the puncture phase, and separates from the lancet body when the drive spring contacts the drive spring catching means during the puncture phase, such that said lancet body continues in the longitudinal puncturing direction while said second end of said drive spring remains stationary against the drive spring catching means with the drive spring under partial tension.

2. The patient's skin puncturing device according to claim 1, wherein, along with said drive spring catching means, said lancet actuation locking means is formed on the additional separate element of said puncturing device.

3. The patient's skin puncturing device of claim 2, wherein the additional separate element comprises a washer, the lancet actuation locking means comprises interlocks, and the drive spring catching means comprises grabs.

4. The patient's skin puncturing device according to claim 1, wherein the housing, the lancet, the push button, the drive spring, the return spring, the lancet actuation locking means, and the drive spring catching means of said puncturing device have dimensions and mutual arrangement that maintain said drive spring after a skin puncture in a tense condition in the retraction phase.

5. The patient's skin puncturing device of claim 1, wherein the first end of the drive spring is configured to move independently of the push button and the second end of the drive spring is configured to move independently of the lancet body.

6. A patient's skin puncturing device for collecting a blood sample comprising:
   a housing having a push-button end portion and a puncturing end portion opposite to the push-button end portion;
   a push button disposed at the push-button end portion of the housing;
   a lancet body disposed inside the housing, wherein the lancet body has a pushing end portion and a needle end portion opposite to the pushing end portion, and wherein the lancet body is configured to move in a longitudinal direction within the housing;
   a puncturing needle disposed at the needle end portion of the lancet body;
   a drive spring disposed between an inner face of the push button and the pushing end portion of the lancet body, wherein the drive spring has a first end portion contacting the inner face of the push button and a second end portion contacting the pushing end portion of the lancet body;
   a return spring disposed between the needle end portion of the lancet body and an internal abutting surface of the puncturing end portion of the housing; and
   a drive spring catch disposed between the second end portion of the drive spring and the puncturing end portion of the housing,
   wherein at a start of a puncture phase with the drive spring compressed between the inner face of the push button and the pushing end portion of the lancet body, the second end portion of the drive spring is spaced longitudinally apart from the drive spring catch, and
   wherein during the puncture phase, the drive spring expands and pushes the lancet body in the longitudinal direction until the second end portion of the drive spring contacts the drive spring catch at which point the pushing end portion of the lancet body separates from the second end portion of the drive spring and continues in the longitudinal direction while the drive spring is held by the drive spring catch under partial tension.

7. The patient's skin puncturing device of claim 6, further comprising a lancet actuation lock, wherein the lancet actuation lock is fixed relative to the housing, and wherein the lancet actuation lock impedes movement of the lancet body in the longitudinal direction at the start of the puncture phase.

8. The patient's skin puncturing device of claim 7, wherein the lancet actuation lock is a breakable projection connected to the housing.

9. The patient's skin puncturing device of claim 7, further comprising a washer of which the drive spring catch and the lancet actuation lock are parts, wherein the washer defines an opening aligned in the longitudinal direction, and wherein the lancet body and the drive spring move through the opening.

10. The patient's skin puncturing device of claim 6, wherein the drive spring catch comprises one or more projections that extend transverse to the longitudinal direction a distance sufficient to impede travel of the drive spring in the longitudinal direction.

11. The patient's skin puncturing device of claim 6, wherein the drive spring catch comprises one or more grab arms extending in the longitudinal direction, each grab arm having a grab projection that extends transverse to the longitudinal direction a distance sufficient to impede travel of the drive spring in the longitudinal direction.

12. The patient's skin puncturing device of claim 6, wherein the drive spring catch is integral with the housing.

13. The patient's skin puncturing device of claim 6, wherein the drive spring is in a compressed condition before, during, and after the puncture phase.

* * * * *